United States Patent
Housman et al.

(10) Patent No.: US 11,648,002 B2
(45) Date of Patent: May 16, 2023

(54) ANCHOR DELIVERY SYSTEMS

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Mark Edwin Housman, North Attleboro, MA (US); Jon-Paul Rogers, North Smithfield, RI (US); Jason Hamilton, Dartmouth, MA (US); Benjamin M. Hall, Roslindale, MA (US); Nehal N. Patel, Boston, MA (US); Rebecca A. Blough, West Warwick, RI (US); Kyle Turner, Mansfield, MA (US)

(73) Assignees: Smith & Nephew, Inc., Memphis, TN (US); Smith & Nephew Orthopaedics AG, Zug (CH); Smith Nephew Asia Pacific Pte. Limited, Singapore (SG)

( * ) Notice: Subject to any disclaimer, the term of this patent is extended or adjusted under 35 U.S.C. 154(b) by 232 days.

(21) Appl. No.: 17/203,881

(22) Filed: Mar. 17, 2021

(65) Prior Publication Data
US 2021/0290218 A1    Sep. 23, 2021

Related U.S. Application Data

(60) Provisional application No. 63/009,632, filed on Apr. 14, 2020, provisional application No. 62/993,322, filed on Mar. 23, 2020.

(51) Int. Cl.
| | | |
|---|---|---|
| *A61B 17/04* | (2006.01) | |
| *A61B 90/00* | (2016.01) | |
| *A61B 17/00* | (2006.01) | |

(52) U.S. Cl.
CPC .. *A61B 17/0401* (2013.01); *A61B 2017/0042* (2013.01); *A61B 2017/044* (2013.01);
(Continued)

(58) Field of Classification Search
None
See application file for complete search history.

(56) References Cited

U.S. PATENT DOCUMENTS

2010/0016869 A1\* 1/2010 Paulk ............... A61B 17/0469
606/232
2010/0069923 A1\* 3/2010 Nguyen ............ A61B 17/0401
606/232

(Continued)

*Primary Examiner* — Alexander J Orkin
(74) *Attorney, Agent, or Firm* — Burns & Levinson LLP; Joseph M. Maraia; Marlo Schepper Grolnic

(57) ABSTRACT

Anchor delivery systems include markings on the surfaces of the delivery device which are visually exposed to the user through openings or fenestrations in the anchor, providing visual feedback to the user on the progress of the anchor's insertion. A suture-locking plug is deformable within the anchor tip, thereby enhancing suture entrapment within the tip of the anchor. A compliant component of the handle places the handle components in tension, thereby absorbing built-in axial looseness in the handle. The handle further includes a spin cavity which allows for free spin of the inserter shaft to finalize insertion of the anchor into bone when the anchor has not been fully seated flush with or below the cortical bone surface.

5 Claims, 13 Drawing Sheets

(52) U.S. Cl.
CPC ......... *A61B 2017/0409* (2013.01); *A61B 2017/0445* (2013.01); *A61B 2090/0807* (2016.02)

(56) References Cited

U.S. PATENT DOCUMENTS

| | | | |
|---|---|---|---|
| 2014/0277128 A1* | 9/2014 | Moore | A61B 17/8875 606/232 |
| 2014/0277129 A1* | 9/2014 | Arai | A61B 17/0401 606/232 |
| 2017/0172562 A1* | 6/2017 | Lombardo | A61B 17/0401 |
| 2019/0350577 A1* | 11/2019 | Norton | A61B 17/0401 |

\* cited by examiner

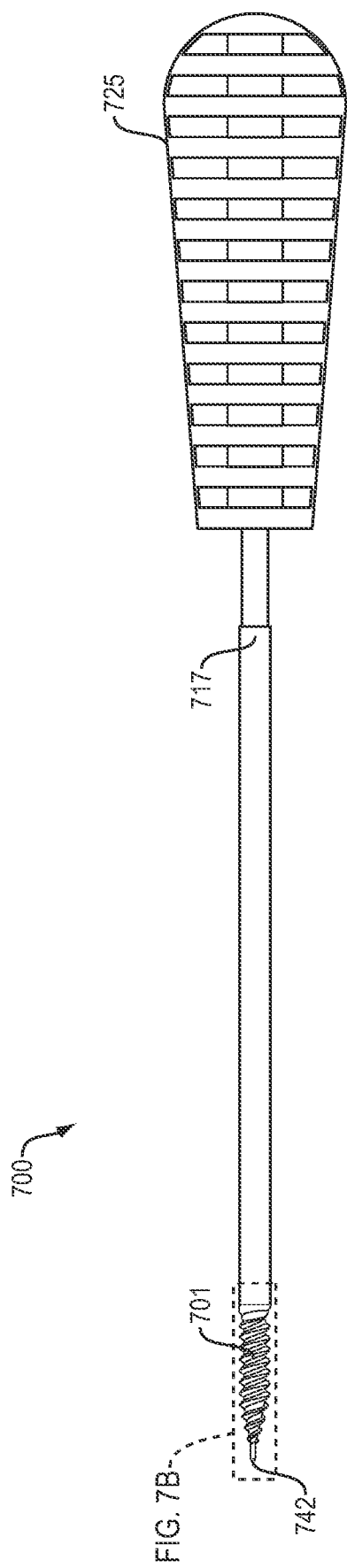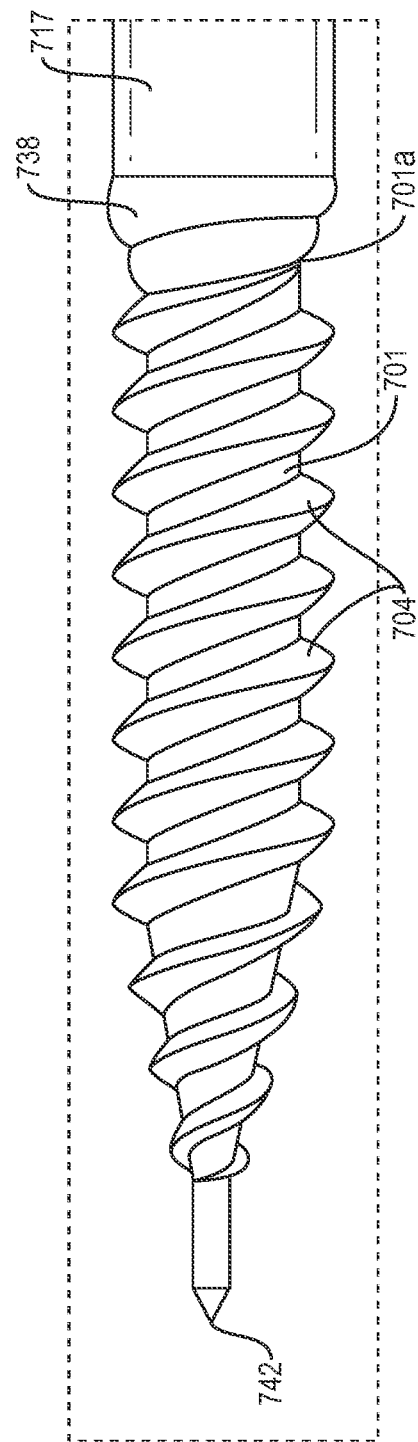
FIG. 7A
FIG. 7B

ANCHOR DELIVERY SYSTEMS

CROSS-REFERENCE TO RELATED APPLICATIONS

This application claims priority to and benefit of U.S. Provisional Application No. 62/993,322, filed Mar. 23, 2020, entitled ANCHOR DELIVERY SYSTEMS, and U.S. Provisional Application No. 63/009,632, filed Apr. 14, 2020, entitled AUTO-MARKING HOLE PREPARATION TOOL, the entire contents of each of which are incorporated herein by reference for all purposes.

BACKGROUND

Arthroscopic procedures often require soft tissue to be reattached to bone. To achieve this, anchors are typically placed in the bone and sutures attached to the anchor are passed through the tissue to securely retain the tissue in place. Typical anchors may be pound-in or screw-in type anchors, or combination anchors having a pound-in distal tip and a screw-in proximal anchor.

Installation of combination pound-in/screw-in type anchors can be problematic due to several issues. One issue is the lack of prominent visual landmarks available to provide feedback to the user on the insertion progress of the anchor. This problem occurs both during the initial pound-in phase of the distal tip as well as during the subsequent screw-in phase of the proximal anchor. Another issue is that some current pound-in/screw-in type anchors include an internal locking plug advanceable within the tip for locking sutures within the tip eyelet. In some cases, insufficient suture retention by the locking plug can allow for the sutures to slip, and thus for the repair construct to loosen and fail.

Another problem with pound-in/screw-in type anchors is that, in instances where there are large amounts of suture loaded into the anchor tip, rotatable parts of the inserter can sometimes reach a travel limit before the screw-in anchor is fully seated into bone. In these cases, the screw-in anchor is left proud of the cortical bone surface, which can lead to irritation of adjacent tissue. This issue is more common with poor quality bone, as the partially implanted anchor cannot finish "pulling" itself into the bone without the mechanical assist of the inserter. In these instances, the bone itself begins to mechanically fail under the loads required to drive the screw-in anchor into the bone hole. Furthermore, while surgeons can choose to abrade the exposed portion of the anchor, this may cause a delay in the progress of the surgery and risk damaging the repair suture.

Another issue with pound-in/screw-in type anchors is that some handles of current anchor delivery systems have an excess of axial clearance between the component parts of the handle, giving an undesirable feeling of looseness within the handle as experienced by the user. Furthermore, if the screw-in portion of the anchor either breaks or pulls out of the bone intraoperatively, it is difficult to remove the distal tip from the repair suture in order to reload the suture into a backup anchor to complete the repair.

SUMMARY

Described herein are anchor delivery systems for combination pound-in/screw-in type anchors which include markings on the surfaces of the delivery device. The markings consist of countdown markers on the driver tip which are visually exposed to the user through openings or fenestrations in the screw-in portion of the anchor. The countdown markers create a countdown sequence for the user, which advantageously provides visual feedback to the user on the progress of the anchor's insertion. Also described herein is a suture-locking plug that is deformable within the anchor tip, and thereby enhances suture entrapment within the tip of the anchor. Additionally, a compliant component of the handle places the handle components in tension, thereby absorbing built-in axial looseness within the handle. In some examples, the handle further comprises a spin cavity which allows for free spin of the inserter shaft to finalize insertion of the screw-in anchor into bone when the screw-in anchor has not been fully seated flush with or below the cortical bone surface. In other examples, a length of internal threads of the delivery device is selected to allow the screw-in anchor to rotate for several turns without threading into the bone while still allowing sufficient axial travel of the screw-in anchor to fully seat into bone. Also disclosed are instruments that can be used by the surgeon to loosen the plug in the anchor tip, allowing for removal of the anchor tip from the repair suture, and to mark the site of a prepared bone hole for easy identification.

Further examples of the anchor delivery systems of this disclosure may include one or more of the following, in any suitable combination.

In examples, the anchor delivery system of this disclosure includes a sleeve body having a proximal end, a distal end, and a plurality of turns of a screw thread extending between the proximal and distal ends. The sleeve body defines an internal volume communicating with a region exterior to the sleeve body through at least one set of axially-aligned openings defined by the sleeve body between adjacent turns of the plurality of turns of screw thread along a length of the sleeve body. A delivery device has an elongated shaft having a proximal portion and a distal portion. The distal portion includes at least one ridge defined by first and second sides of the shaft. At least one of the first and second sides has a series of axially-aligned markings extending along a length of the at least one of the first and second sides. When the sleeve body is engaged with the distal portion of the shaft, each marking of the series of axially-aligned markings of the delivery device is visible through a respective opening of the at least one set of axially-aligned openings of the sleeve body, providing a user with visual feedback on insertion progress of the sleeve body into bone.

In further examples, the internal volume of the sleeve body includes at least one slot extending between the proximal and distal ends of the sleeve body. When the sleeve body is engaged with the distal portion of the shaft, the at least one ridge of the delivery device is engageable with the at least one slot of the sleeve body. In examples, the at least one slot is four slots. Each slot is spaced about 90° around a surface of the internal volume of the sleeve body from another slot. In examples, the at least one set of axially-aligned openings is two sets of axially-aligned openings, and the at least one slot is positioned between the two sets of axially-aligned openings. In examples, the at least one set of axially-aligned openings is four sets of axially-aligned openings. Each set of axially-aligned openings is spaced about 90° around a circumference of the sleeve body from another set of axially-aligned openings. In examples, the at least one ridge is four ridges. Each ridge is spaced about 90° around a surface of the shaft of the delivery device from another ridge. In examples, the at least one set of axially-aligned markings is a set of numerals. In examples, the set of numerals includes five numerals which count down in a stepwise fashion by odd numbers from the distal end to the proximal end of the shaft. In other examples, the set of numerals includes four numerals which count down in a stepwise fashion by even numbers from the distal end to the proximal end of the shaft. In examples, the at least one set of axially-aligned openings is five axially-aligned openings. In other examples, the at least one set of axially-aligned openings is four axially-aligned openings.

In further examples, the anchor delivery system of this disclosure includes a tip having a distal portion and a proximal portion. The proximal portion defines a cavity therein with a wall of the cavity having threads. An eyelet is defined in the distal portion of the tip in communication with the cavity. A plug has a threaded outer portion and an internal cannulation configured for receipt of an inner shaft of a delivery device. The plug is disposed within the cavity of the tip such that threads of the threaded outer portion are engaged with the threads of the cavity. The plug is rotatable and axially moveable through the cavity by rotation of the inner shaft to engage a suture threaded through the eyelet. When the inner shaft of the delivery device is disposed within the cannulation of the plug, a length of the inner shaft is selected such that a gap is formed between a distal end of the inner shaft and a distal end of the cannulation. The gap provides a crushable zone such that a distal end of the plug is deformable when the plug is engaged with the suture in the eyelet. In yet further examples, a proximal portion of the plug extends from the cavity of the tip. In other examples, the tip is coupled to an intermediate shaft of the delivery device such that the inner shaft extends through the intermediate shaft. In further examples, the plug includes a non-threaded outer portion. The non-threaded outer portion is distal to the threaded outer portion.

In other examples, the anchor delivery system of this disclosure includes a handle assembly including a handle grip. An outer shaft extends from a distal end of the handle assembly. A proximal end of the outer shaft is coupled to an outer shaft hub. A sleeve advancement member is at least partially disposed within the handle assembly. A proximal end of the sleeve advancement member defines a rotatable knob adjacent a proximal end of the handle assembly. A distal end of the sleeve advancement member is operatively coupled to the outer shaft hub such that rotation of the rotatable knob causes rotational movement of the outer shaft. A drive housing is at least partially disposed within the sleeve advancement member. An anti-rotation member is coupled to the handle grip and the drive housing for preventing rotation of the handle grip during rotation of the rotatable knob. A length and stiffness of the anti-rotation member is selected to force the drive housing, the sleeve advancement member and the handle grip into axial contact to eliminate axial looseness in the handle assembly.

In other examples, an anchor delivery system of this disclosure includes a handle assembly including a handle grip. An outer shaft extends from a distal end of the handle assembly. A proximal end of the outer shaft is coupled to an outer shaft hub. A sleeve advancement member is at least partially disposed within the handle assembly. A proximal end of the sleeve advancement member defines a rotatable knob adjacent a proximal end of the handle assembly. A distal end of the sleeve advancement member is operatively coupled to a center housing having internal threads configured to engage outer threads on the outer shaft hub, such that rotation of the rotatable knob causes rotational movement of the outer shaft. At an end of an axial travel limit of the outer shaft hub along the internal threads of the center housing, the outer shaft hub is configured to freely rotate within a non-threaded portion of the center housing. In further examples, the system includes an anti-rotation member coupled to the handle grip and a drive housing at least partially disposed within the sleeve advancement member. The anti-rotation member is configured to prevent rotation of the handle grip during rotation of the rotatable knob.

In further examples, an anchor delivery system of this disclosure includes a handle assembly including a handle grip. A first shaft is coupled to the handle assembly. A proximal end of the first shaft coupled to a hub and a distal end of the first shaft is coupled to an anchor sleeve. A second shaft extends through the first shaft. A distal end of the second shaft is coupled to a tip having a proximal portion and a distal portion. A sleeve advancement member is at least partially disposed within the handle assembly. A proximal end of the sleeve advancement member defines a rotatable knob adjacent a proximal end of the handle assembly. A distal end of the sleeve advancement member is operatively coupled to a center housing having internal threads configured to engage outer threads on the hub such that rotation of the rotatable knob causes rotational movement of the first shaft. A length of the internal threads of the center housing is selected to exceed a distance between a distal end of the anchor sleeve and the distal portion of the tip.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIGS. 7A-C illustrate a hole preparation tool for use with the anchor delivery systems of this disclosure.

DETAILED DESCRIPTION

Figure 1A:
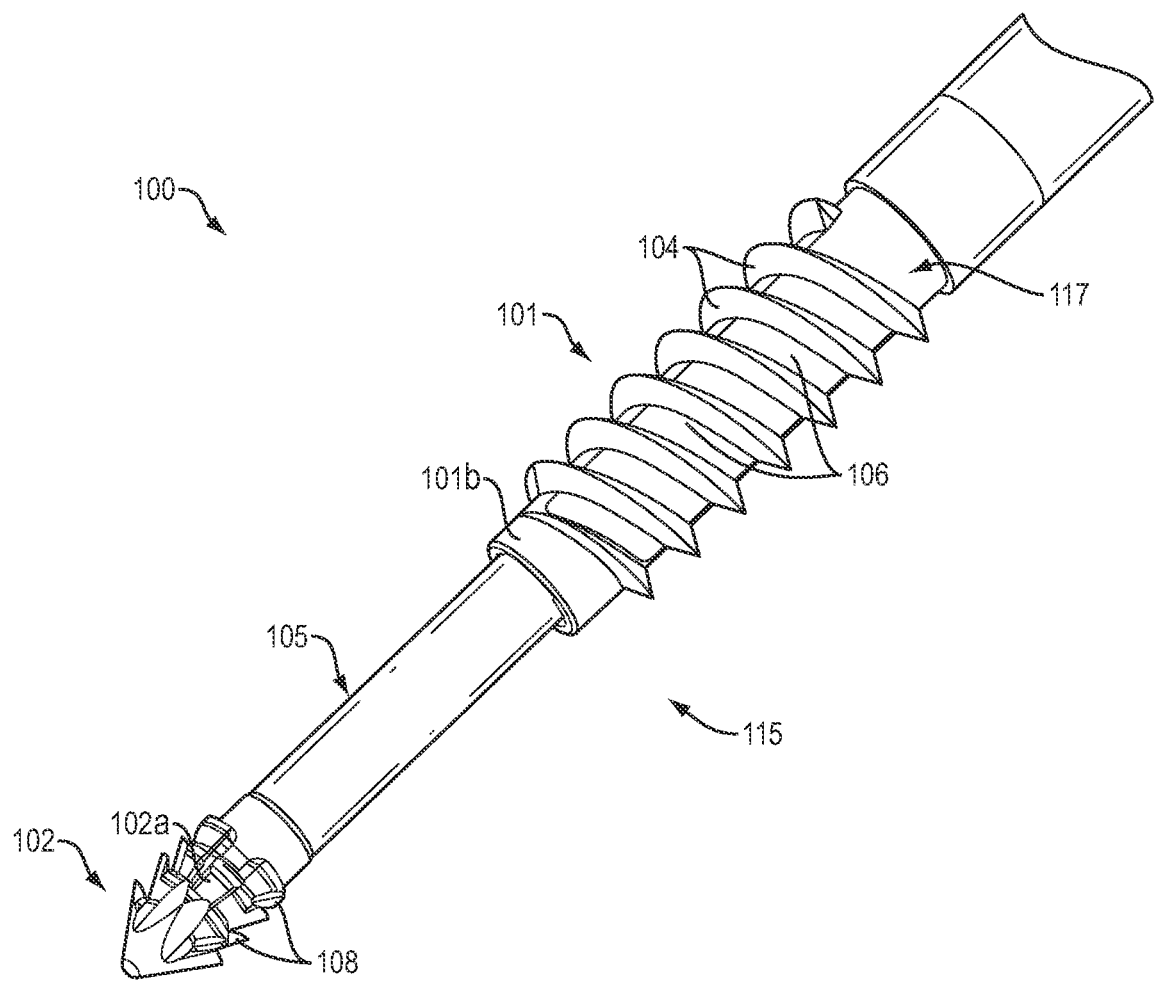
FIGS. 1A and 1B illustrate a prior art anchor delivery system.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Figure 1B:
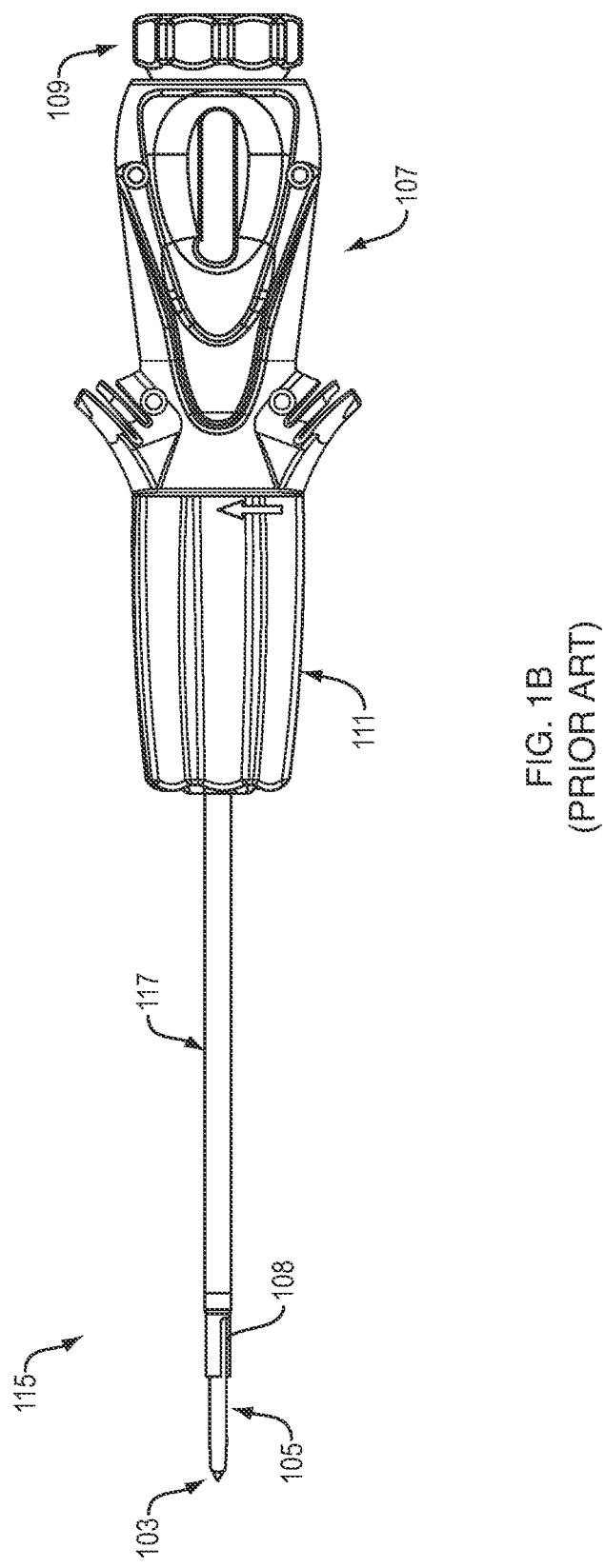

For a better understanding of the current disclosure, FIGS. 1A and 1B depict a prior art anchor delivery system 100 for securing a tissue to bone. As shown in FIG. 1A, the anchor delivery system 100 generally includes a screw-in type anchor sleeve 101 and a pound-in type tip 102. In examples, the anchor sleeve 101 includes a plurality of turns of a screw thread 104 having a plurality of openings 106 between turns of the plurality of turns of a screw thread 104 for allowing bony ingrowth from the bone into an internal volume defined within the plurality of turns of a screw thread 104. In examples, the tip 102 includes a suture capture member, such as a plug (not shown), advanceable through an internal cavity of the tip 102 to lock one or more sutures in an eyelet 102a extending through the tip 102. In examples, the tip 102 may include barbs 108 protruding therefrom to improve pullout strength of the tip 102. However, in other examples, the tip 102 may be smooth-sided. In examples, the anchor sleeve 101, the tip 102 and the plug can be constructed from polymers (e.g., PEEK), bioabsorbable materials, metals (e.g., surgical steel, titanium), or any other suitable material.

As shown in more detail in FIG. 1B, the anchor sleeve 101 and the tip 102 can be installed into bone using a delivery device 115. The delivery device 115 generally includes an outer shaft 117 for engaging with the anchor sleeve 101, an inner shaft 103 for engaging with the plug of the tip 102, and a handle assembly 107 for holding and operating the delivery device 115. In examples, the delivery device 115 can also include one or more intermediate shafts 105 to provide additional stiffness when pounding in the tip 102. In examples, the internal volume of the anchor sleeve 101 may comprise longitudinal ribs to engage grooves or slots 108 extending along the outer shaft 117. In other examples, the outer shaft 117 may comprise longitudinal ribs (not shown) to engage recesses extending through the internal volume of the anchor sleeve 101. In some examples, the anchor sleeve 101 is screwed or otherwise advanced by the outer shaft 117 into bone over a proximal end of the tip 102 by rotation of a sleeve advancement member 111. In examples, a suture capture knob 109 is operatively coupled to a proximal end of the inner shaft 103 such that rotating or twisting the suture capture knob 109 causes the inner shaft 103 to advance the plug within the eyelet 102a of the tip 102. Additional non-limiting examples of anchor delivery systems can be found in U.S. Pat. No. 9,526,488, to Smith & Nephew, Inc. (Memphis, Tenn.), the entire contents of which are incorporated herein by reference.

Figure 2A:
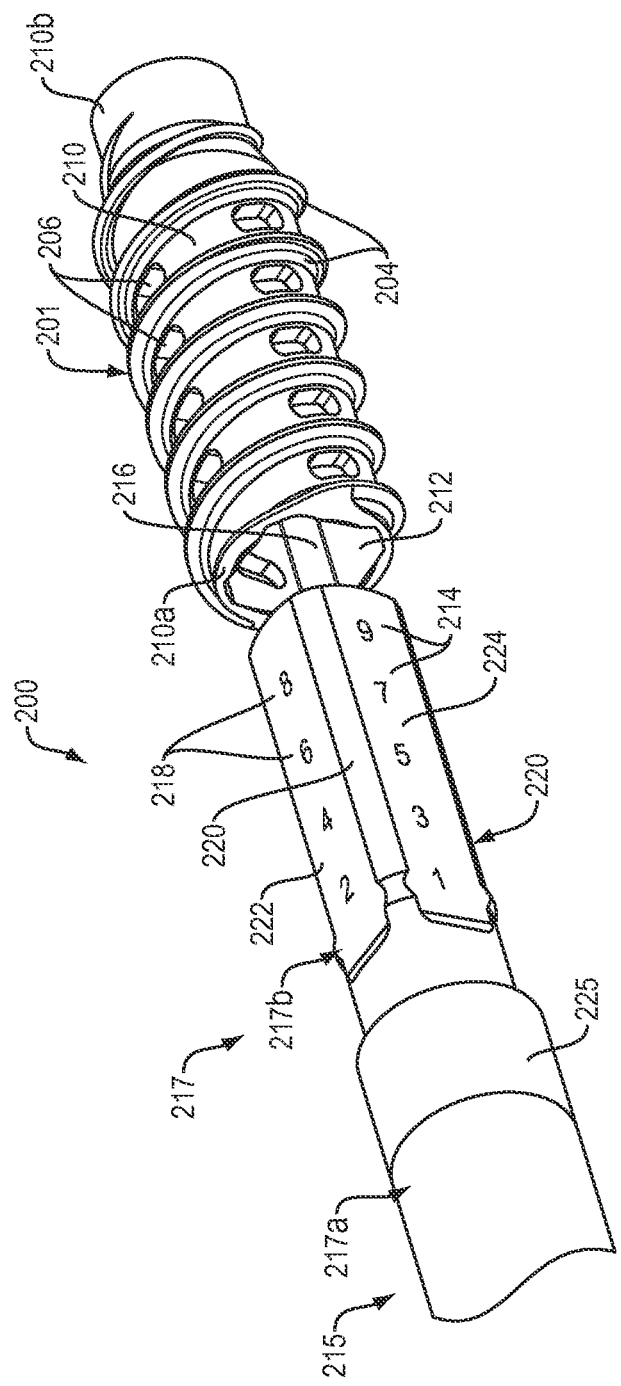
FIG. 2A illustrates an anchor sleeve portion of an anchor delivery system of this disclosure in an exploded view.

Turning now to FIG. 2A, an example of an anchor delivery system 200 of this disclosure is shown in an exploded, perspective view. The anchor delivery system 200 may be used to insert an anchor sleeve 201 and a tip, such as tip 102, into bone. As shown in FIG. 2A, the anchor delivery system 200 includes a delivery device 215 having an outer shaft 217 for engaging with the anchor sleeve 201. The anchor sleeve 201 comprises a substantially cylindrical sleeve body 210 having a proximal end 210a, a distal end 210b, and a plurality of turns of a screw thread 204 extending between the proximal end 210a and the distal end 210b. In examples, the distal end 210b of the sleeve body 210 can include a non-threaded portion, as shown. The sleeve body 210 defines an internal volume 212 which communicates with an exterior of the sleeve body 210 through at least one set axially-aligned openings 206 defined by the portions of the sleeve body 210 extending between adjacent turns of the screw thread 204. In examples, four sets of axially-aligned openings 206 are defined by the sleeve body 210. However, more or fewer than four sets of axially-aligned openings 206 are contemplated by this disclosure. Each set of axially-aligned openings 206 are spaced about 90° from another set of axially-aligned openings 206 around a circumference of the sleeve body 210. The sleeve body 210 also includes at least one slot 216 disposed within the internal volume 212 and extending between the proximal end 210a and the distal end 210b of the sleeve body 210. In examples, the sleeve body 210 includes four slots 216. However, more or fewer than four slots 216 are contemplated by this disclosure. Each slot 216 is spaced about 90° from another slot 216 around a surface of the interior volume 212 and is disposed between adjacent sets of axially-aligned openings 206.

Still referring to FIG. 2A, the outer shaft 217 of the delivery device 215 includes a proximal portion 217a and a distal portion 217b. An outer surface of the distal portion 217b includes a plurality of ridges 220 extending a length of the distal portion 217b. In examples, the distal portion 217b includes four ridges 220. However, more or fewer than four ridges 220 are contemplated by this disclosure. Each ridge 220 is spaced about 90° from another ridge 220 around an outer surface of the outer shaft 217 and is defined by two substantially flat sides 222, 224 extending along a length of the ridge 220. Side 224 includes a first set of axially-aligned, laser-marked numerals 214, while side 222 includes a second set of axially-aligned, laser-marked numerals 218, the purpose of which will be described in more detail below. Each ridge 220 is configured to engage a respective slot 216 of the anchor body 210 when the distal portion 217b of the delivery device 215 is inserted into the interior volume 212 of the anchor body 210.

Figure 2B:
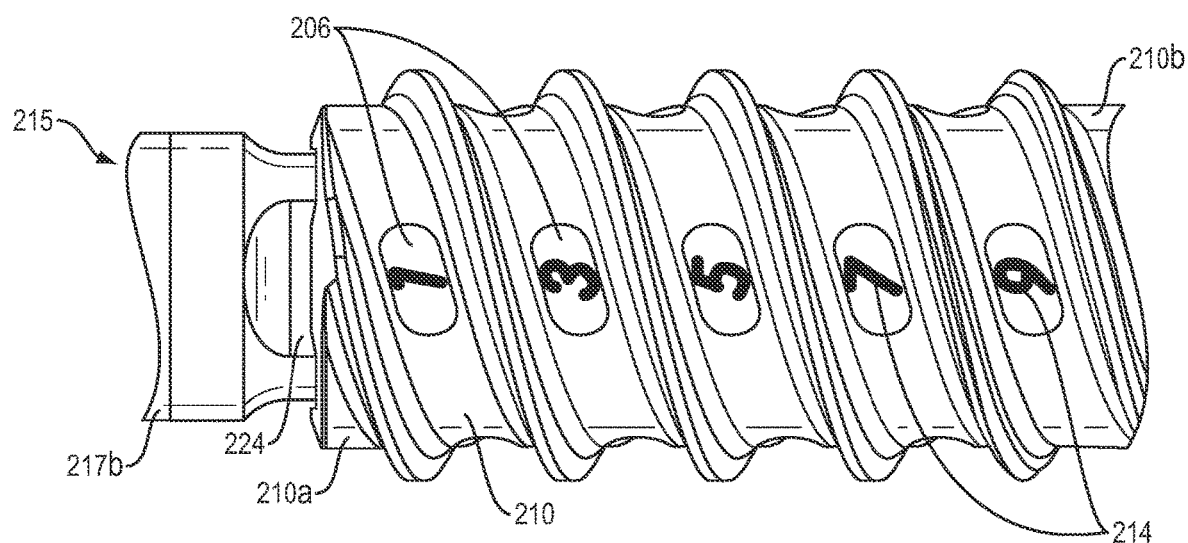
FIGS. 2B and 2C are detailed illustrations of the anchor sleeve portion of FIG. 2A in an assembled view.
Figure 2C:
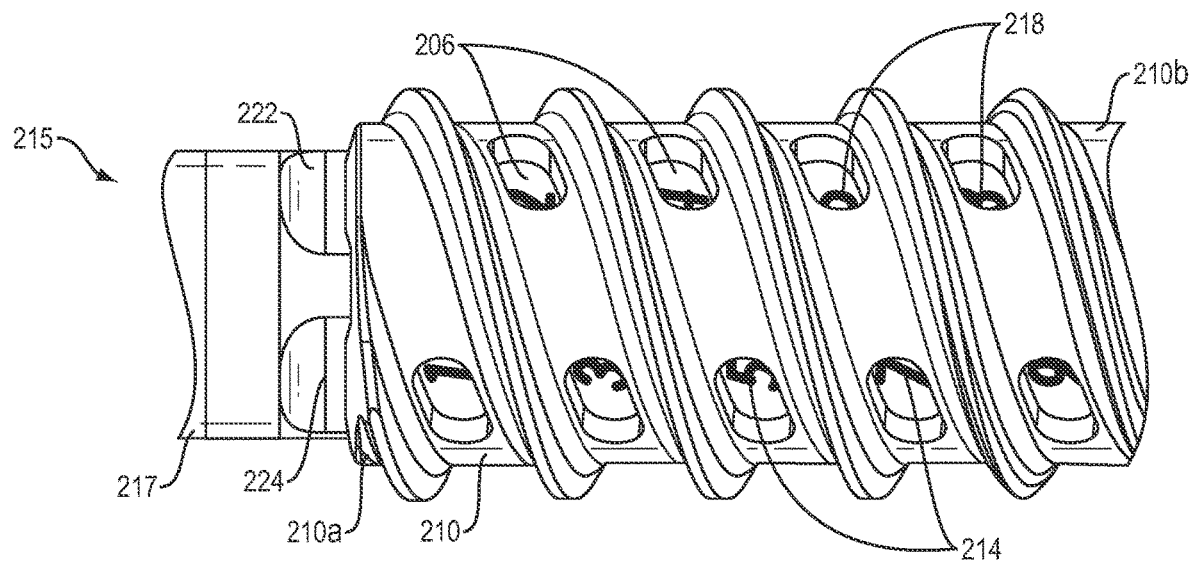

Turning now to FIG. 2B, a detailed view of the sleeve body 210 and the distal portion 217b of the delivery device 215 is shown in an assembled view. In FIG. 2B, the first set of laser marked numerals 214, which may be five numerals 214, on the side 224 of the delivery device 215, are visible through a first set of axially-aligned openings 206 of the sleeve body 210. The first set of numerals 214 count down in a stepwise fashion by odd numbers (e.g., 9, 7, 5, 3, 1) from the distal end 210b to the proximal end 210a of the sleeve body 210. FIG. 2C shows the sleeve body 210 of FIG. 2B rotated clockwise by about ⅛ of a turn. As seen in FIG. 2C, the second set of laser marked numerals 218, which may be four numerals, on the side 222 of the delivery device 215, are visible through a second set of axially-aligned openings 206 of the sleeve body 210. The second set of numerals 218 count down in a stepwise fashion by even numbers (e.g., 8, 6, 4, 2) from the distal end 210b to the proximal end 210a of the sleeve body 210. In use, as the sleeve body 210 is inserted into bone via rotation of the outer shaft 217, the first set of numerals 214 and second set of numerals 218 give the user visual feedback that the sleeve body 210 is inserting into bone, rather than merely free-spinning.

It will be appreciated that, if the sleeve body 210 of FIG. 2C were again rotated clockwise, a third set of laser marked numerals, which may be five numerals, on an opposite side of the delivery device 215 from side 224, would be visible through a third set of axially-aligned openings 206 of the sleeve body 210. The third set of numerals would count down in a stepwise fashion by odd numbers from the distal end 210b to the proximal end 210a of the sleeve body 210. If the sleeve body 210 of FIG. 2C were further rotated clockwise, a fourth set of laser marked numerals, which may be four numerals, on an opposite side of the delivery device 215 from side 222, would be visible through a fourth set of axially-aligned openings 206 of the sleeve body 210. The fourth set of numerals would count down in a stepwise fashion by even numbers from the distal end 210b to the proximal end 210a of the sleeve body 210. It is also contemplated by this disclosure that, rather than numerals, other visual markings could be used to indicate the insertion progress of the anchor body 210 into bone. For example, the markings could be a sequence of alternating characters, such as dots and dashes. In other examples, the markings could be a sequence of dots of changing size, number and/or shape. In further examples, the markings could be a series of dash lines with a changing azimuth angle.

Figure 3A:
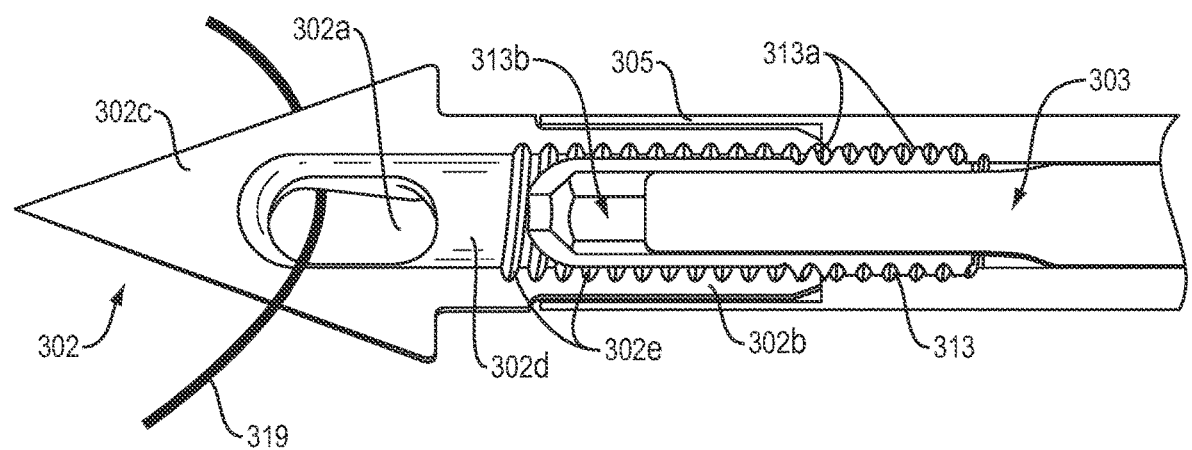
FIGS. 3A and 3B are detailed illustrations of a distal tip portion of another example of an anchor delivery system of this disclosure in a cross-sectional view.

Turning now to FIG. 3A, examples of a tip 302, an inner shaft 303, an intermediate shaft 305, and a locking plug 313 are illustrated in a cross-sectional, detailed view. In examples, the tip 302 includes a distal portion 302c and a proximal portion 302b. A tip cavity 302d is defined within the proximal portion 302b of the tip 302 and is configured to receive the plug 313 through an opening in the proximal portion 302b. The eyelet 302a extends through the distal portion 302c of the tip 302 and is in communication with the tip cavity 302d. In examples, a distal end of the tip 302 may be pointed as shown, for creation of a bone hole. However, it contemplated by this disclosure that the distal end of the tip 302 may be blunt in cases where a bone hole is created prior to insertion of the tip 302. The plug 313 includes an internal cannulation 313b extending through the plug 313, while an outer surface of the plug 313 includes threads 313a. In examples, the threads 313a extend an entire length of the plug 313. In other examples, as shown, only a proximal portion of the plug 313 is threaded, while a distal portion of the plug 313 is unthreaded. The tip cavity 302d includes threads 302e that engage the threads 313a of the plug 313 upon insertion of a portion of the plug 313 into the tip cavity 302d. In examples, the remainder of the plug 313 extends outside of the tip cavity 302d.

Figure 3B:
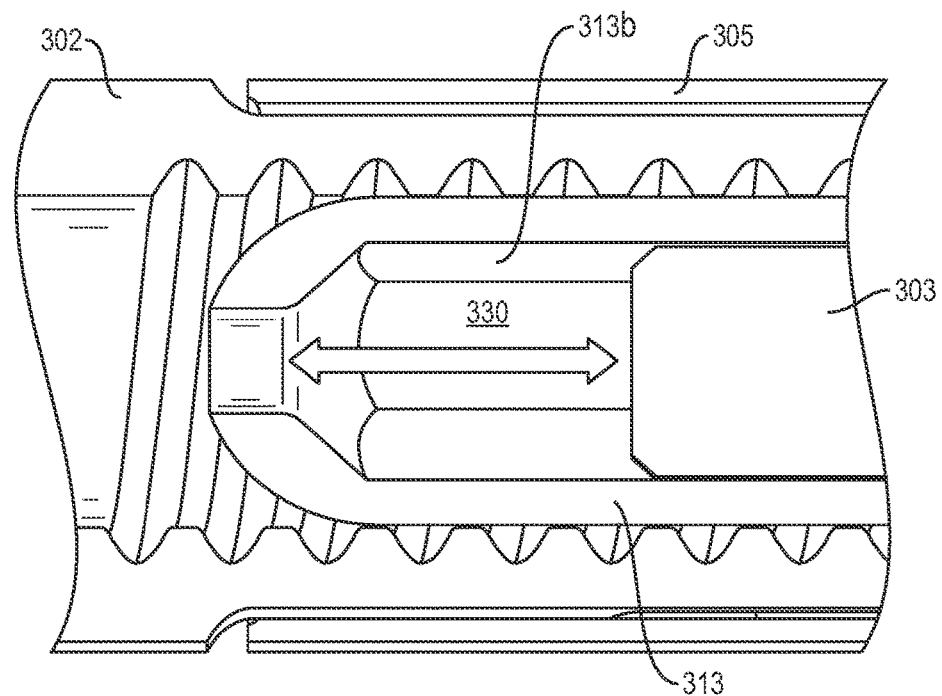

Still referring to FIG. 3A, when engaged with the delivery device, the proximal portion 302b of the tip 302 is coupled to the intermediate shaft 305, and the inner shaft 303 extends through the intermediate shaft 305 for engagement with the internal cannulation 313b of the plug 313. In examples, the internal cannulation 313b of the plug 313 and a mating portion of the inner shaft 303 having a corresponding geometry, such as a hexagonal shape. During tissue repair, sutures 319 attached to soft tissue (not shown) are placed through the eyelet 302a of the tip 302. A length of the inner shaft 303 is selected such that a gap or void 330 (FIG. 3B) is formed between the distal end of the inner shaft 303 and the distal end of the internal cannulation 313b of the plug 313. The void 330 may be empty of material, or may be filled with a material having a lower density than the plug 313. The void 330 thus provides a crushable zone at the distal end of the plug 313 which allows the distal end of the plug 313 to be deformable. In use, the tip 302 is placed within a bone hole (not shown) via axial advancement, such as malleting, of the delivery device. The suture capture knob 109 of the delivery device 115 (FIG. 1B) is rotated to move the plug 313 via the inner shaft 303 distally into the eyelet 302a where the plug 313 encounters the sutures 319. As the plug 313 and the inner shaft 303 are descended further into the eyelet 302a, the plug 313 impinges on the sutures 319 with a force sufficient to deform the distal end of the plug 313 around the sutures 319, thus allowing for more surface contact between the sutures 319 and the plug 313. The increased surface contact between the plug 313 and the sutures 319 advantageously allows for more friction and holding force on the sutures 319 by the plug 313 within the eyelet 302a.

Figure 4A:
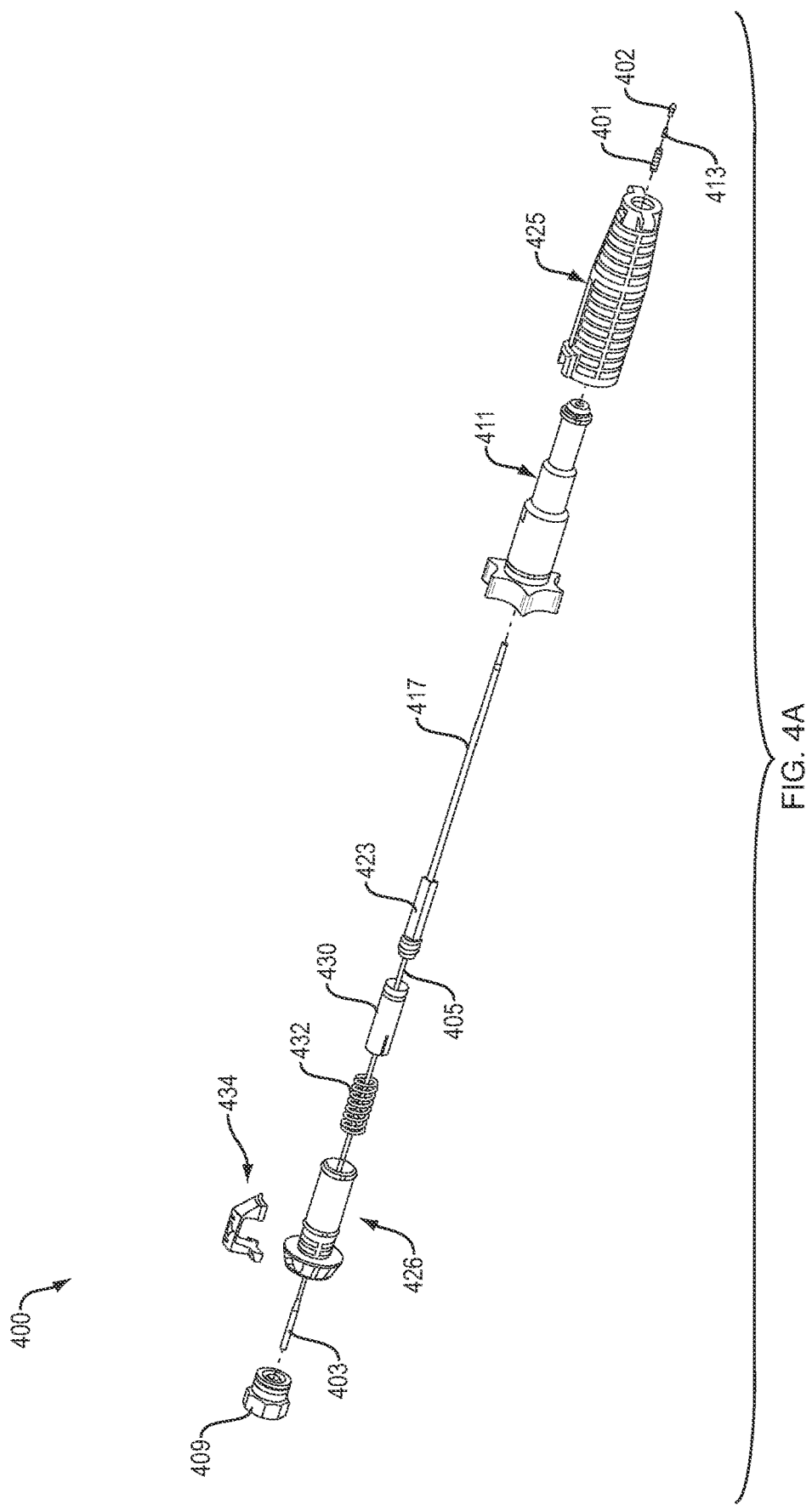
FIG. 4A illustrates another example of an anchor delivery system of this disclosure in an exploded view.

Turning now to FIG. 4A, an example of an anchor delivery system 400 of this disclosure is shown in a perspective, exploded view. The anchor delivery system 400 may be used to insert an anchor sleeve 401 and a tip 402 into bone. As shown in FIG. 4A, the anchor delivery system 400 includes an outer shaft 417 for engaging with the sleeve 401, and an intermediate shaft 405 extending through the outer shaft 417 for engaging with the tip 402. A proximal end of the outer shaft 417 is coupled to an outer shaft hub 423. The outer shaft hub 423 in turn is configured to be threadingly coupled to a center housing 430. The anchor delivery system 400 also includes a drive housing 426 for holding the intermediate shaft 405. The anchor delivery system 400 furthermore includes a suture capture knob 409 coupled to the inner shaft 403 for advancing the plug 413 within the tip 402, a sleeve advancement member 411 for screwing the anchor sleeve 401 into bone, and a handle grip 425 for holding and/or maneuvering the anchor delivery system 400 during insertion of the anchor sleeve 401 into bone. A spring 432 is configured to be disposed within the drive housing 426 to allow a relative motion between the outer shaft 417 and the inner shaft 403, thereby absorbing at least a portion of the impact forces exerted on the sleeve 401 during the pounding-in of the tip structure 402. The anchor delivery system 400 may also include an anti-rotation feature, such as a bridge 434, which is described in more detail below.

Figure 4B:
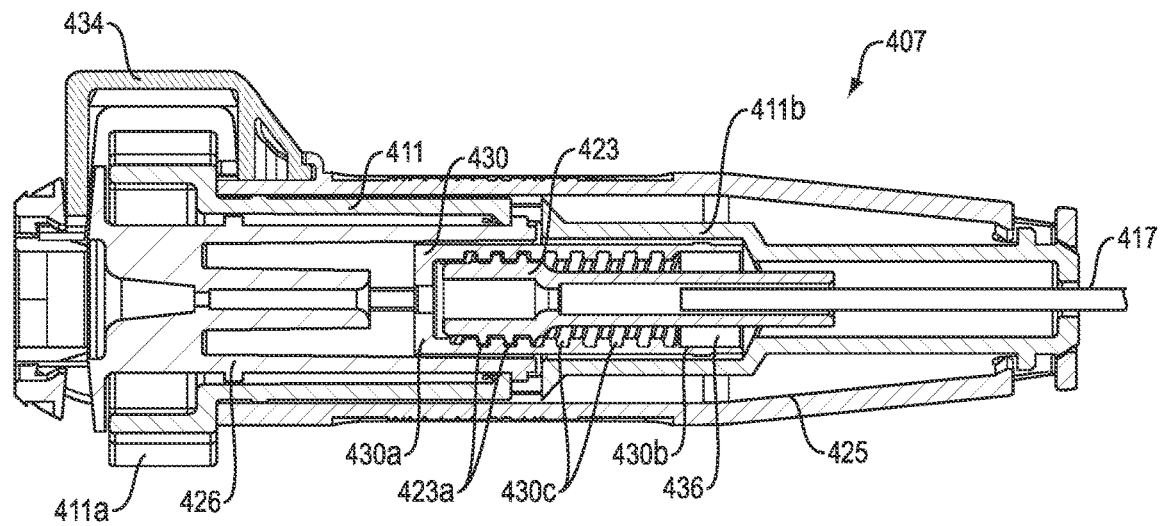
FIGS. 4B and 4C illustrate the handle assembly of the anchor delivery system of FIG. 4A in cross-sectional views.

FIG. 4B shows the internal components of the handle assembly 407 of the delivery device 415 of FIG. 4A in a cross-sectional view. In particular, FIG. 4B shows the sleeve advancement member 411 and the handle grip 425. A proximal end of the sleeve advancement member 411 defines a rotatable knob 411a extending outside of the handle grip 425 near the proximal end of the handle assembly 407. In examples, a proximal portion 430a of the center housing 430 may have internal threads 430c for engaging threads 423a on an outer surface of the outer shaft hub 423. A distal portion 430b of the center housing 430 may be unthreaded, forming a "spin cavity" 436, the purpose of which will be described in more detail below. The outer shaft hub 423 can be further engaged with a distal end 411b of the sleeve advancement member 411. Thus, twisting or rotating the sleeve advancement member 411 via the rotatable knob 411a rotates the outer shaft hub 423, thereby causing the outer shaft hub 423 to advance distally along the threads 430c of the center housing 430 and, consequently, to cause the outer shaft 417 to advance the sleeve 401 into engagement with bone and/or the tip 402.

Still referring to FIG. 4B, the bridge 434 is configured to stabilize the handle grip 425 to the drive housing 426, preventing the handle grip 425 from rotating during rotation of the sleeve advancement member 411. In their natural state, the bridge 434, the drive housing 426, the sleeve advancement member 411 and the handle grip 425 have built-in axial clearances to prevent these components from binding during use. Therefore, in the handle assembly 407 of this disclosure, a length of the bridge 434 is selected to place the bridge 434 in compression, like a spring. This compression causes the axial clearances between the components to be absorbed as the drive housing 426, the sleeve advancement member 411 and the handle grip 425 are forced into axial contact. Specifically, the force generated by the bridge 434 being placed in compression forces the drive housing 426 and the handle grip 425 away from each other. The force generated by the bridge 434 being placed in compression is counteracted in the flexure joint between the sleeve advancement member 411 and the drive housing 426, and in the flexure joint between the handle grip 425 and the sleeve advancement member 411. The quantity of the axial force exerted by the bridge 434 is a function of the amount of built-in interference between the bridge 434 and the other components and by the stiffness of the bridge 434. Thus, a stiffness of the bridge 434 is selected such that a range of acceptable, non-zero axial loads are generated by the handle assembly 407 with the currently defined component tolerances. These generated axial loads advantageously remove axial clearance from the components of the handle assembly 407, thus eliminating a feeling of looseness in the handle assembly 407 as experienced by the user. It is also contemplated by this disclosure that other compression mechanisms than the bridge 434 could be used to axially load the handle assembly 407. In addition, the amount of interference could be set on each individual handle assembly 407 with shims (not shown) to closely tune the compression force and feel of each individual handle assembly 407.

Figure 4C:
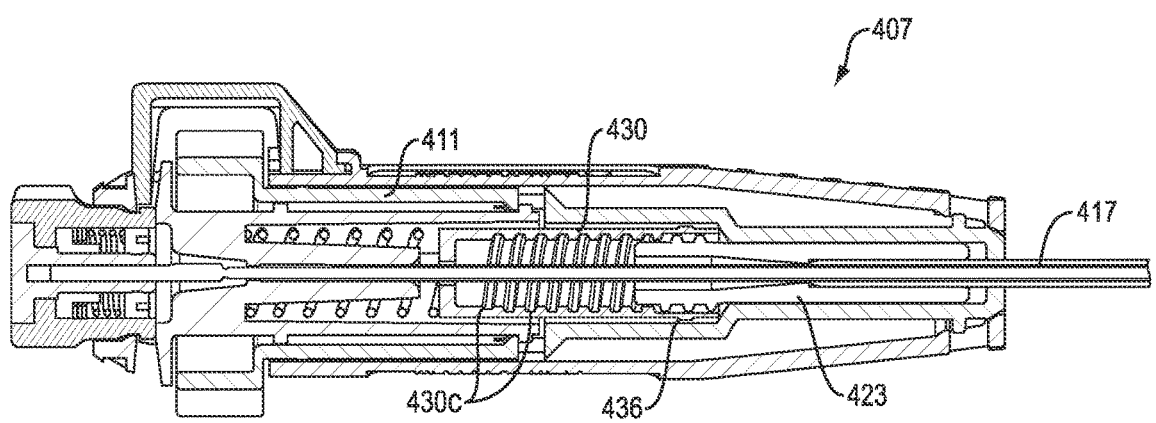

Turning now to FIG. 4C, in some cases, some of the available travel of the outer shaft hub 423 within the center housing 430 is consumed while the anchor sleeve 401 spins at the bone surface without entering the bone. This can prevent the anchor sleeve 401 from being fully seated flush with or below the cortical bone surface, which is the desired outcome. Thus, in the handle assembly 407 of this disclosure, at the end of the distal travel of the outer shaft hub 423 within the center housing 430, the outer shaft hub 423 is configured to fully unthread from the threads of the center housing 430 and freely rotate within the spin cavity 436. If the anchor sleeve 401 has not been fully seated flush with or below the cortical surface of bone, the free rotation of the outer shaft hub 423 within the spin cavity 436 may be sufficient to complete the insertion of the anchor sleeve 401 into bone. It is further contemplated that the threads may be entirely eliminated from both of the center housing 430 and the outer shaft hub 423, and that the free spinning of the outer shaft hub 423 within the center housing 430 is sufficient to insert the anchor sleeve 401 into bone.

Figure 5A:
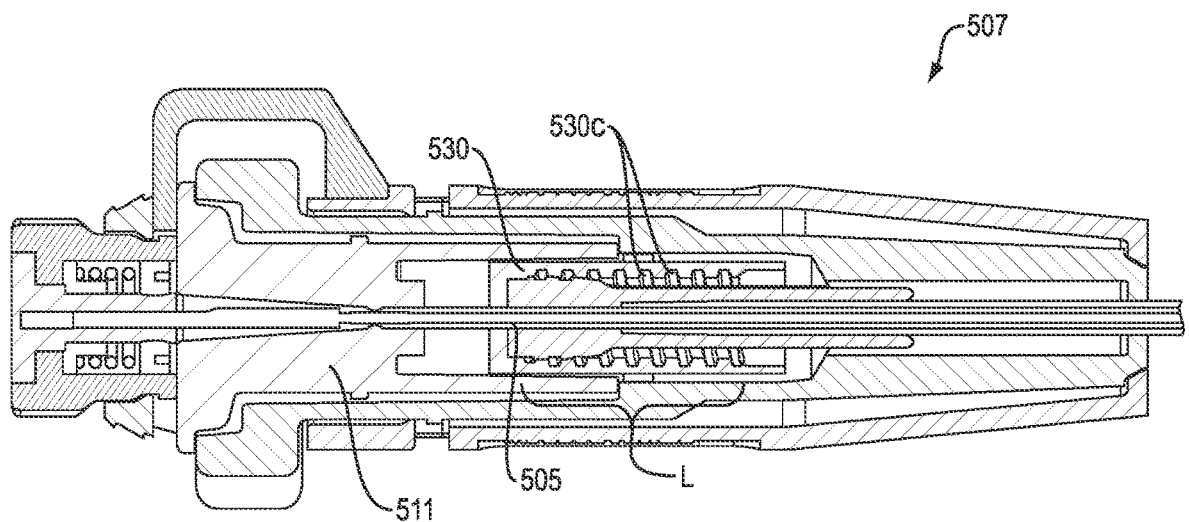
FIGS. 5A and 5B illustrate another handle assembly of the anchor delivery system of this disclosure.
Figure 5B:
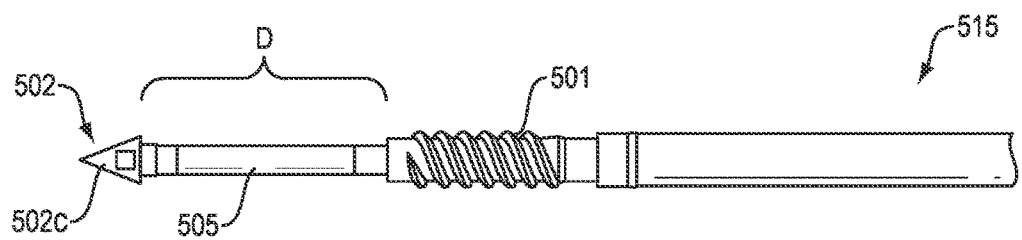

Turning to FIG. 5A, another example of a handle assembly 507 of this disclosure is shown in a cross-sectional view. In the handle assembly 507, a length L of the threads 530c of the center housing 530 is selected to exceed a staging distance D between the distal end of the anchor sleeve 501 and the distal portion 502c of the tip 502 (FIG. 5B). The length L of the threads 530c allows the anchor sleeve 501 to undergo more handle-driven advancement, helping to address the issue of leaving the anchor sleeve 501 proud of the bone or tissue. In use, the user first inserts the tip 502 into a bone hole. The user then activates the plug (for example, plug 313, 413) into the tip 502 prior to inserting the anchor sleeve 501 into engagement with the tip 502. Activating the plug releases the tip 502 from the intermediate shaft 505 of the delivery device 515. If the anchor sleeve 501 rotates without inserting into bone, the mechanical action of the delivery device 515 will withdraw the intermediate shaft 505 from the bone hole. However, because the tip 502 has been released from the intermediate shaft 505, the tip 502 generally remains at its fully deployed, distal location. The user can then rotate the anchor sleeve 501 without the anchor sleeve 501 threading into the bone for several turns of the sleeve advancement member 511 without fear of running out of mechanically assisted axial travel from the delivery device 515. In examples, the threads 530c of the center housing 530 can be longer or shorter as long as the total length L of the threads 530c exceeds the distance D between the anchor sleeve 501 and the distal portion 502c of the tip 502.

Figure 6A:
FIGS. 6A and 6B illustrate an unlocking instrument for use with the anchor delivery systems of this disclosure.
Figure 6B:
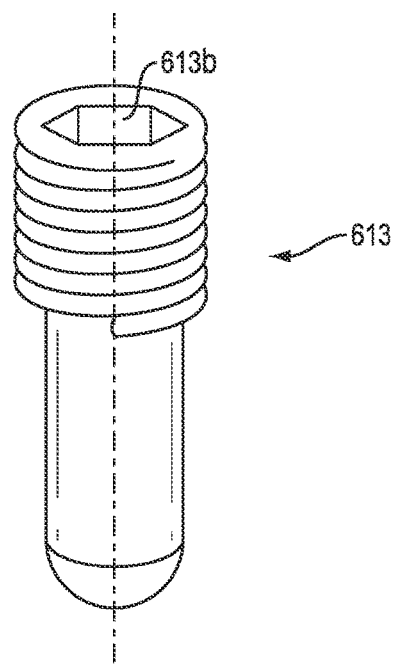

Turning now to FIG. 6A, an example of an unlocking instrument 600 of this disclosure for use with the anchor delivery systems 100, 200, 400 is shown in a side view. The unlocking instrument 600 is configured for removing a tip 602 from a suture 619 after the tip 602 has been deployed into bone. The unlocking instrument 600 has a similar working length to the working lengths of the anchor delivery systems 100, 200, 400 described above. As shown in FIG. 6A, the unlocking instrument 600 comprises a handle 625 and a shaft 603 extending from the handle 625. In examples, the handle 625 is made for single-use and is comprised of injection molded plastic. In other examples, the handle 625 is reusable and comprised of stainless steel. A distal end of the shaft 603 comprises a hex feature 660 configured to mate with the hexagonal cannulation 613b of the plug 613 (FIG. 6B). Thus, the unlocking instrument 600 is used to loosen the contact between the plug 613 and the suture 619 secured within the tip 602, allowing for removal of the tip 602 from the suture 619.

Figure 6C:
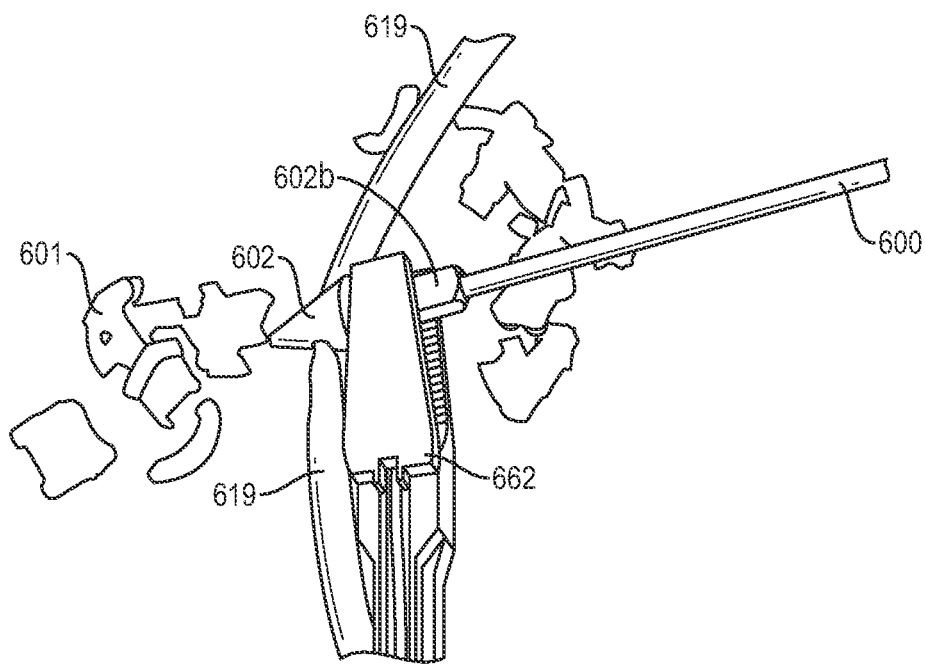
FIGS. 6C and 6D illustrate the use of the unlocking instrument of FIGS. 6A and 6B.
Figure 6D:
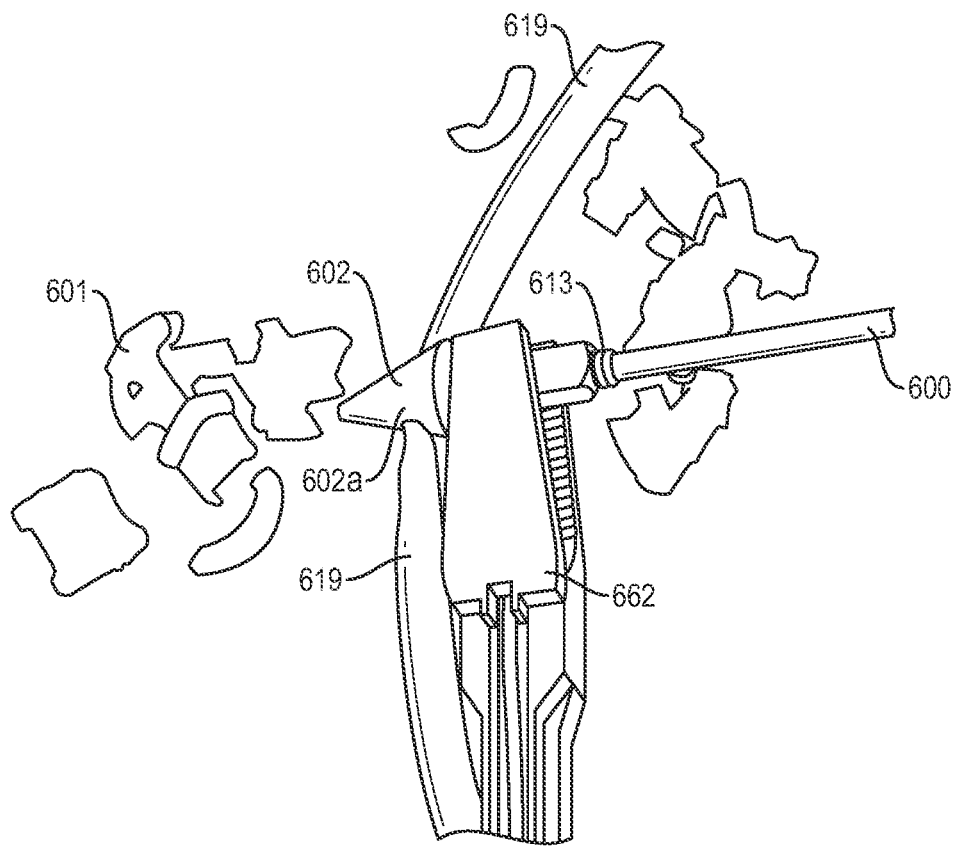

Turning now to FIG. 6C, in use, an instrument such as a grasper tool 662 is introduced into a repair site in which, for example, the anchor sleeve 601 has broken after insertion into bone. The tip 602 is held with the grasper tool 662 to stabilize the tip 602 during removal of the plug 613. The unlocking instrument 600 is then inserted into the proximal end 602b of the tip 602. As shown in FIG. 6D, the hex feature 660 of the unlocking instrument 600 is then engaged with the cannulation 613b of the plug 613. Once the unlocking instrument 600 is engaged with the plug 613, the unlocking instrument 600 is rotated to loosen the contact between the plug 613 and the suture 619 which has been threaded through the eyelet 602a. With the plug 613 loosened, the user can use the grasper tool 662 (or other means) to hold and slide the tip 602 off of the suture 619 and retrieve the tip 602 from the repair site. The user is then free to use a replacement anchor sleeve/tip with the suture 619 to complete the repair. It is also contemplated by this disclosure that the unlocking instrument 600 could also include a mechanism (not shown) for gripping the tip 602 during removal of the plug 613.

Figure 7C:
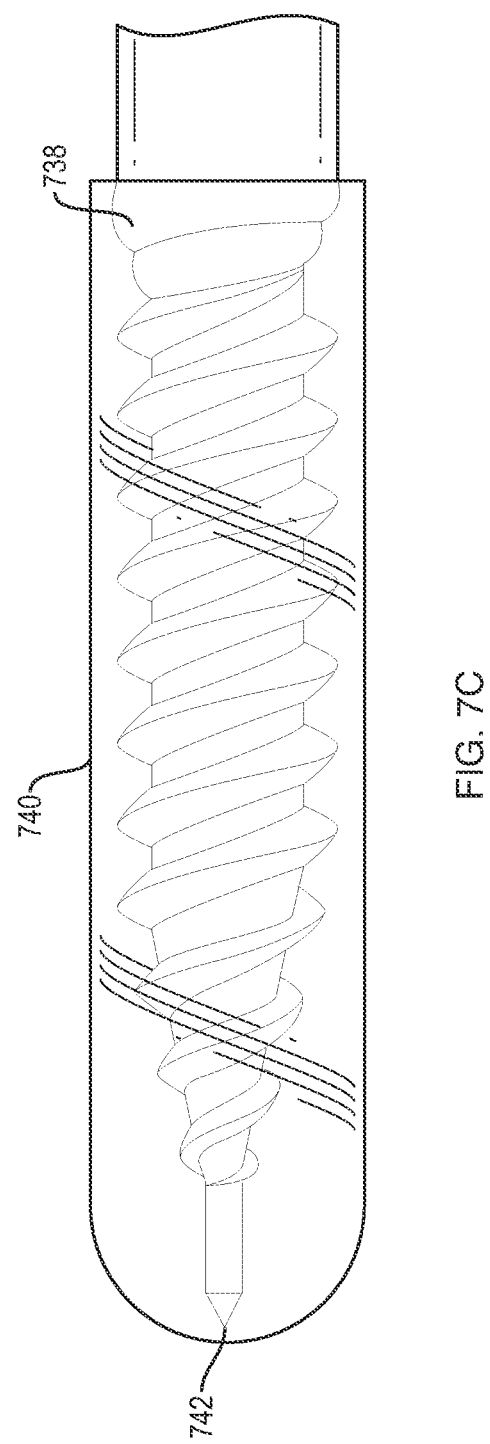

Turning now to FIGS. 7A and 7B, an example of a hole preparation tool 700 of this disclosure for use with the anchor delivery systems 100, 200, 400 is shown in a side view (FIG. 7A) and a detailed view (FIG. 7B). As shown in FIGS. 7A and 7B, the hole preparation tool 700 includes a handle grip 725 and a shaft 717 extending from the handle grip 725. In examples, the shaft 717 includes a distal pointed tip 742 for piercing bone. A threaded portion 701 of the hole preparation tool 700 may include a plurality of turns of a screw thread 704 for pre-tapping a bone hole before insertion of a threaded anchor sleeve. The hole preparation tool 700 also includes a marking element 738 disposed around the shaft 717 adjacent to a proximal end 710a of the threaded portion 701. In examples, the marking element 738 comprises an absorbent material pre-saturated with surgical ink. In examples, the marking element 738 has an annular shape, as shown. However, the disclosure contemplates other suitable shapes of the marking element 738, including two half-annuli. As shown in FIG. 7C, to protect the tip 742 from puncturing surrounding packaging and to protect the marking element 738 from drying out, a protective cap 740 covers the tip 742 as well as the marking element 738 of the bone preparation tool 700.

Figure 7D:
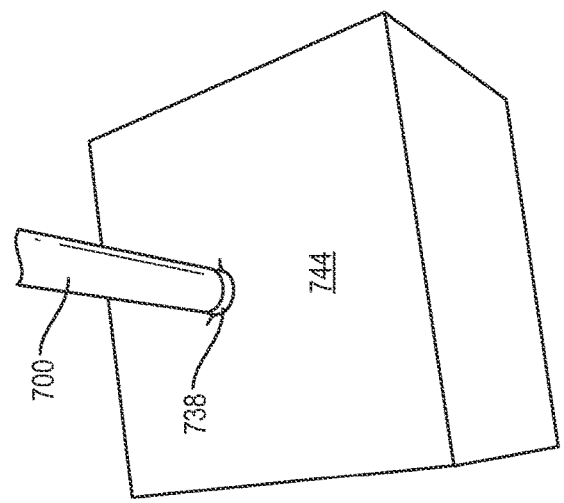
FIGS. 7D-G illustrate the use of the hole preparation tool of FIGS. 7A-C.
Figure 7E:
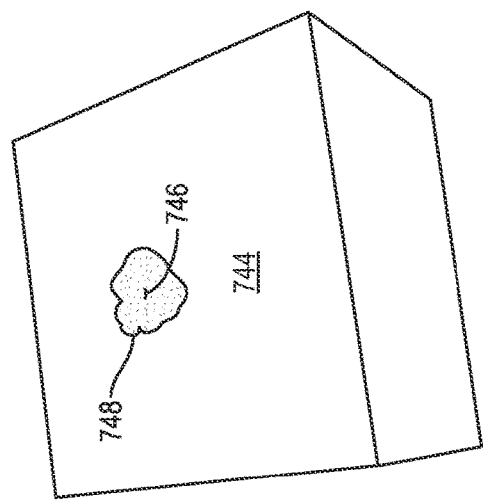
Figure 7F:
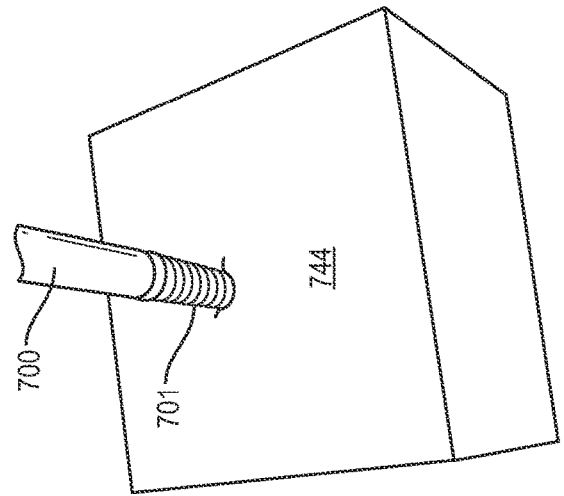
Figure 7G:
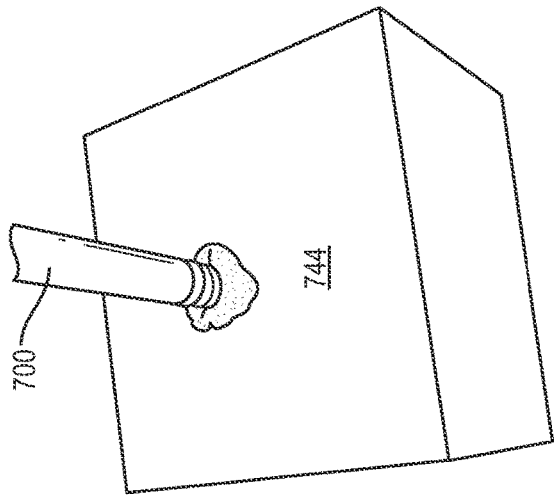

FIGS. 7D-G illustrate an example using the hole preparation tool 700 in a surgical repair. As shown in FIG. 7D, a surgeon first inserts the tip 742 of the hole preparation tool 700 into bone 744. Next, as shown in FIG. 7E, the surgeons rotates the hole preparation tool 700 to advance the threaded portion 701 into the bone 744 until the marking element 738 comes into contact with the surface of the bone 744. When the marking element 738 contacts the surface of the bone 744, the marking element 738 marks the bone 744 with ink. As shown in FIG. 7F, the surgeon then unthreads the hole preparation tool 700 and removes it from the repair site, leaving behind a prepared bone hole 746 and an ink mark 748 identifying the location of the prepared bone hole 746 (FIG. 7G). The disclosure also contemplates other methods of marking the bone hole 746, including using radio-frequency energy.

While the disclosure has been particularly shown and described with references to preferred examples thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

The invention claimed is:

1. An anchor delivery system comprising:
a handle assembly including a handle grip;
an outer shaft extending from a distal end of the handle assembly, a proximal end of the outer shaft coupled to an outer shaft hub;
a sleeve advancement member at least partially disposed within the handle assembly, a proximal end of the sleeve advancement member defining a rotatable knob adjacent a proximal end of the handle assembly, a distal end of the sleeve advancement member operatively coupled to the outer shaft hub such that rotation of the rotatable knob causes rotational movement of the outer shaft;
a drive housing at least partially disposed within the sleeve advancement member; and
an anti-rotation member coupled to the handle grip and the drive housing for preventing rotation of the handle grip during rotation of the rotatable knob;
wherein a length and stiffness of the anti-rotation member is selected to force the drive housing, the sleeve advancement member and the handle grip into axial contact to eliminate axial looseness in the handle assembly.

2. The anchor delivery system of claim 1, wherein the anti-rotation member is a bridge member coupled to an outer surface of the handle assembly.

3. The anchor delivery system of claim 1, further comprising an intermediate shaft extending through the outer shaft.

4. The anchor delivery system of claim 1, wherein the outer shaft hub is configured to threadingly engage interior threads of a center housing for movement along the center housing.

5. The anchor delivery system of claim 4, wherein a distal portion of the center housing is unthreaded such that the outer shaft hub freely spins within the unthreaded distal portion.

* * * * *